US012419997B2

(12) United States Patent
Wong et al.

(10) Patent No.: US 12,419,997 B2
(45) Date of Patent: Sep. 23, 2025

(54) OSTOMY BAG WITH A SLIPPERY SURFACE

(71) Applicant: The Penn State Research Foundation, University Park, PA (US)

(72) Inventors: Tak-Sing Wong, University Park, PA (US); Jing Wang, University Park, PA (US); Birgitt Boschitsch, University Park, PA (US)

(73) Assignee: The Penn State Research Foundation, University Park (PA)

( * ) Notice: Subject to any disclaimer, the term of this patent is extended or adjusted under 35 U.S.C. 154(b) by 1238 days.

(21) Appl. No.: 17/083,863

(22) Filed: Oct. 29, 2020

(65) Prior Publication Data

US 2021/0052784 A1 Feb. 25, 2021

Related U.S. Application Data

(63) Continuation of application No. PCT/US2019/031408, filed on May 9, 2019.
(Continued)

(51) Int. Cl.
*A61L 31/14* (2006.01)
*A61F 5/445* (2006.01)
(Continued)

(52) U.S. Cl.
CPC .............. *A61L 31/14* (2013.01); *A61F 5/445* (2013.01); *A61L 31/10* (2013.01); *C08G 77/24* (2013.01);
(Continued)

(58) Field of Classification Search
CPC .......... A61L 31/14; A61L 5/445; A61L 31/10; A61L 2400/10; A61L 2420/02; A61L 2420/08; C08G 77/24
See application file for complete search history.

(56) References Cited

U.S. PATENT DOCUMENTS

| 7,651,485 B2 | 1/2010 | Fattman |
| 8,343,121 B2 | 1/2013 | Cramer et al. |

(Continued)

FOREIGN PATENT DOCUMENTS

| WO | 2014012080 A1 | 1/2014 |
| WO | 2016183102 A1 | 11/2016 |
| WO | 2017176709 A1 | 10/2017 |

OTHER PUBLICATIONS

English machine translation for WO2017169466 (Year: 2017).*
(Continued)

*Primary Examiner* — Michael C Miggins
(74) *Attorney, Agent, or Firm* — DINSMORE & SHOHL LLP

(57) ABSTRACT

An ostomy bag having a polymeric surface is prepared by forming a polyphenol layer on the surface, forming a silanization layer on the polyphenol layer and forming a lubricant layer entrenched over the silanization layer. The silanization layer is polymerized from a solution including: (i) a polymerizable silane or siloxane or combination thereof; (ii) a solvent; and (iii) an acid catalyst. The silanization layer comprises an array of silanes or siloxanes or a combination thereof each having ends anchored to the polyphenol layer and opposite ends extending away from the polyphenol layer.

19 Claims, 8 Drawing Sheets

Related U.S. Application Data

(60) Provisional application No. 62/671,054, filed on May 14, 2018.

(51) Int. Cl.
  *A61L 31/10* (2006.01)
  *C08G 77/24* (2006.01)

(52) U.S. Cl.
  CPC ....... *A61L 2400/10* (2013.01); *A61L 2420/02* (2013.01); *A61L 2420/08* (2013.01)

(56) References Cited

U.S. PATENT DOCUMENTS

| | | |
|---|---|---|
| 9,707,120 B2 | 7/2017 | Nguyen-DeMary et al. |
| 10,105,255 B2 | 10/2018 | Fattman et al. |
| 2014/0206630 A1* | 7/2014 | Messersmith .......... B01D 15/08 427/256 |
| 2014/0242516 A1 | 8/2014 | Ogawa et al. |
| 2014/0342954 A1 | 11/2014 | Ingber et al. |
| 2017/0224876 A1 | 8/2017 | Babcock et al. |

OTHER PUBLICATIONS

International Search Report dated Jul. 17, 2019; International Application PCT/US19/31408.
Extended European Search Report dated Dec. 21, 2021; International Application EP19803794.

* cited by examiner

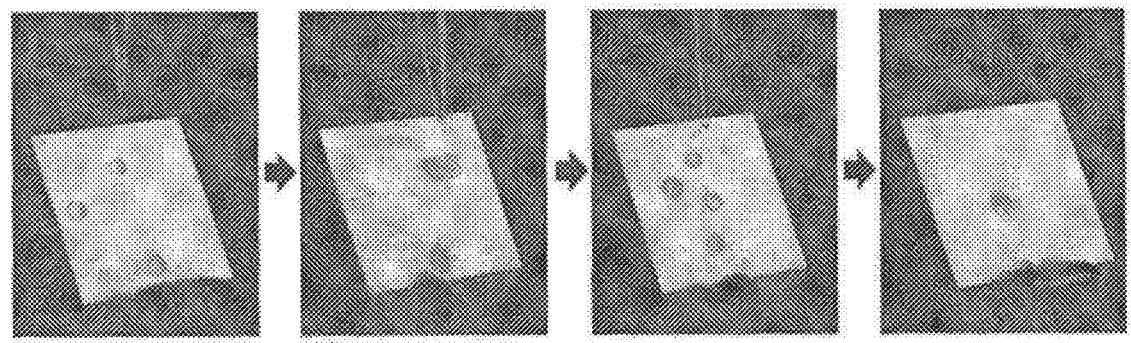
Polystyrene — Figure 2a
After soaking Polyphenol — Figure 2b
After silanization — Figure 2c
After Lubrication — Figure 2d
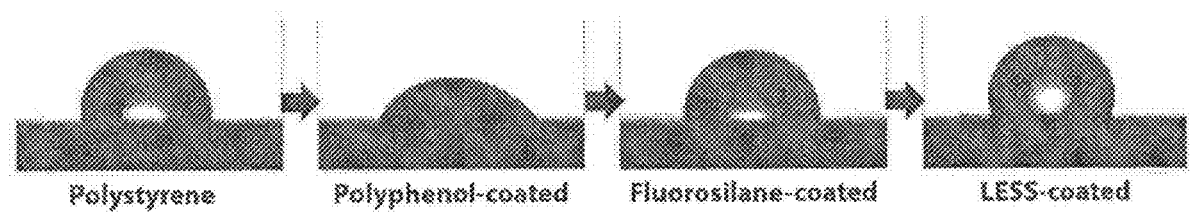
Polystyrene — Figure 3a
Polyphenol-coated — Figure 3b
Fluorosilane-coated — Figure 3c
LESS-coated — Figure 3d

OSTOMY BAG WITH A SLIPPERY SURFACE

CROSS-REFERENCE TO RELATED APPLICATION

This application is a continuation of International Patent Application No. PCT/US2019/031408 filed May 9, 2019 and designating the United States of America and which claims the benefit of U.S. Provisional Application No. 62/671,054 filed 14 May 2018, the entire disclosure of both are hereby incorporated by reference in their entirety.

STATEMENT REGARDING FEDERALLY SPONSORED RESEARCH

This invention was made with government support under Grant No. CMMI1351462 awarded by the National Science Foundation. The Government has certain rights in the invention.

FIELD OF THE INVENTION

The present disclosure relates to ostomy bags having slippery surfaces and methods of making ostomy bags having slippery surfaces, particularly liquid-entrenched smooth surfaces (LESS) that can be challenging to be chemically functionalized on materials such as polymers. The methods disclosed herein can be applied to, without limitation, personal protective equipment such as face shields, aeration membranes, catheters, menstrual cups, etc.

BACKGROUND OF THE INVENTION

An ostomy bag is used to be secured to the abdomen of a patient for collecting bodily waste in connection with surgery for a number of diseases in the gastro-intestinal or urinary tract. These bodily waste materials may be gases, liquids, solids and semi-solid waste. It is desirable in any event to dispose the collected materials with minimal handling from the user. For the regions and areas where medical supplies are in short supply, ostomy bags often may be reused. It is desired that the internal surface of ostomy bags can have self-cleaning and anti-fouling functions which facilitate emptying the waste and bring comfort and convenience to the users.

Self-cleaning and anti-fouling surfaces are in high demand for their nature of keeping themselves clean. There are various self-cleaning surfaces in nature, such as lotus leaf, butterfly wings, pitch plant rim, etc. These plant or animal surfaces mainly use two mechanisms to form their self-cleaning property: (1) an air cushion is created by combining micro/nano surface structures and hydrophobic surface chemistry (e.g. lotus leaf); or (2) a liquid layer is created by combining surface structure and hydrophilic or oleophilic surface chemistry (e.g. pitcher plant rim).

In the past two decades, many engineered self-cleaning surfaces have been created by using these two mechanisms, such as superhydrophobic surfaces, superoleophobic surfaces, slippery liquid-infused surfaces (SLIPS), and so on. See, e.g., Lafuma, Superhydrophobic states. *Nat. Mater.* 2, 457-460 (2003); Tuteja et al., Designing Superoleophobic Surfaces. *Science* 318, 1618-1622 (2007); Wong et al., Bioinspired self-repairing slippery surfaces with pressure-stable omniphobicity. *Nature* 477, 443-447 (2011).

Some engineered surfaces are fabricated with complex processes, involving cleanroom fabrication, hazardous chemicals, and considerable labor and time. Some artificial self-cleaning surfaces have already been used from daily activities (e.g. water-resistance smartphones) to industrial applications.

Repellent and biofouling-free coatings on medical materials, such as catheters, have also been described. See MacCallum, et al., Liquid-infused silicone as a biofouling-free medical material, Biomaterials Science & Engineering 2015 (1):43-51; and Geyer et al., How to coat the inside of narrow and long tubes with a super-liquid-repellent layer—A promising candidate for antibacterial catheters.

Several patent applications further describe repellent and anti-biofouling coatings. Such patent applications include, for example, WO2018094161 to Wong et al., WO2013106588 to Ingber et al., US 2018/0187022 to Aizenberg et al.

However, it remains a challenge to develop a simple scalable process to form slippery surfaces over a wide variety of substrate materials, which need to repel various liquids, sticky viscoelastic solids, and biological matters, such as water, crude oil, human feces, blood and tissue, etc.

Accordingly, there is a need for new surface technology that provides a simple universal coating method to create self-cleaning coatings on most types of solids surfaces to repel a wide range of materials, including liquids and viscoelastic solids.

SUMMARY OF THE INVENTION

The present disclosure provides an ostomy bag with a slippery surface which can be self-cleaning and anti-fouling. Embodiments of the present invention provide methods for forming a slippery surface for an ostomy bag, where the slippery surface is a polymeric surface including a polyphenol layer on the surface, a silanization layer on the polyphenol layer and a lubricant layer entrenched over the silanization layer. The silanization layer comprises an array of silanes or siloxanes or a combination thereof each having ends anchored to the polyphenol layer and opposite ends extending away from the polyphenol layer. The silanization layer may be polymerized from a solution including: (i) a polymerizable silane or siloxane or combination thereof; (ii) a solvent; and (iii) an acid catalyst.

Advantages of the present disclosure include substrates with slippery and antifouling surfaces and a process that can be applied universally to a variety of substrates including plastics, metals, ceramic and glass to form the slippery surfaces. Such surfaces can advantageously repel both liquids and viscoelastic semi-solids and solids (e.g., viscoelastic materials) for a variety of applications. In addition, processes of the present disclosure advantageously can be carried out with relatively simple equipment and conditions which allow for large scale and economically favorable manufacture.

These and other advantages are satisfied, at least in part, by a substrate having a slippery surface comprising a layer of polyphenol on a surface of the substrate, a silanization layer directly on the polyphenol layer, and a lubricant over the silanization layer. Advantageously, the polyphenol layer adheres to the substrate surface and provides free hydroxyl groups that can react with a silane or siloxane or both to form covalent bonding of a silanization layer directly thereto. A stable lubricant layer can be applied over the silanization layer which could be entrenched in the silanization layer, i.e., the lubricant layer would be over and within the silanization layer and adhere to the silanization layer.

Embodiments of the present disclosure include one or more of the following features individually or combined.

For example, the substrate surface can have an average roughness of less than 1 μm; the silanization layer can include an array of straight-chain (i.e., linear) polysilanes or polysiloxanes or a combination thereof having ends anchored to the polyphenol layer and opposite ends extending away from the polyphenol layer; the silanization layer can be attached to the polyphenol layer by either condensation polymerization of monomers or through direct attachment of linear polymers; the lubricant can be one or more of an omniphobic lubricant, a hydrophobic lubricant, e.g., a silicone oil or plant oil, or a perfluorinated oil, and/or a hydrophilic lubricant. In some embodiments, the polyphenol layer can have a thickness of less than about 100 nm, such as less than about 50 nm, e.g., less than about 7 nm. In other embodiments, the silanization layer can have a thickness of less than about 50 nm, such as less than about 20 nm, e.g., less than about 7 nm. In still further embodiments, the silanization layer can comprise an array of straight-chain polydimethylsiloxane polymers, a $C_{1-30}$ perfluoroalkyl silane, and/or a $C_{1-30}$ alkylsilane and the lubricant can comprise one or more of silicone oils, mineral oils, plant oils, and/or perfluorinated oils.

Another aspect of the present disclosure includes a process for preparing a substrate with a slippery surface. The process includes forming a polyphenol layer on a surface of a substrate; forming a silanization layer directly on the formed polyphenol layer; and forming a stable lubricant layer over the silanization layer to form the slippery surface.

Embodiments include any one or more of the features described for the slippery surface and/or any one or more of the following features, individually or combined. For example, the polyphenol layer can be formed by applying a solution including a polyphenol on to the surface of the substrate and drying the solution; the polyphenol layer can also be formed by applying a solution including one or more phenols and reacting the phenols to form the polyphenol layer on the surface. In other embodiments, the silanization layer is formed directly on the polyphenol layer by polymerizing a silane or siloxane or a combination thereof to form an array of linear polysilanes and/or polysiloxanes polymers, wherein the array of linear polymers have ends anchored to the polyphenol layer and opposite ends extending away from the polyphenol layer. Advantageously, an array of linear polysilanes and/or polysiloxanes polymers can be polymerized from a solution applied to the polyphenol layer on the substrate, wherein the solution includes: (i) a polymerizable silane or siloxane or combination thereof, (ii) a solvent and (iii) an acid catalyst.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIGS. 2a-2d show images of liquid repellency and hydrophobicity changes of a polystyrene sheet before and after various treatments of the surface of the sheet;

FIGS. 3a-3d show images of a water drop on the polystyrene sheet before and after various treatment of the surface of the sheet;

DETAILED DESCRIPTION OF THE INVENTION

Figure 1A:
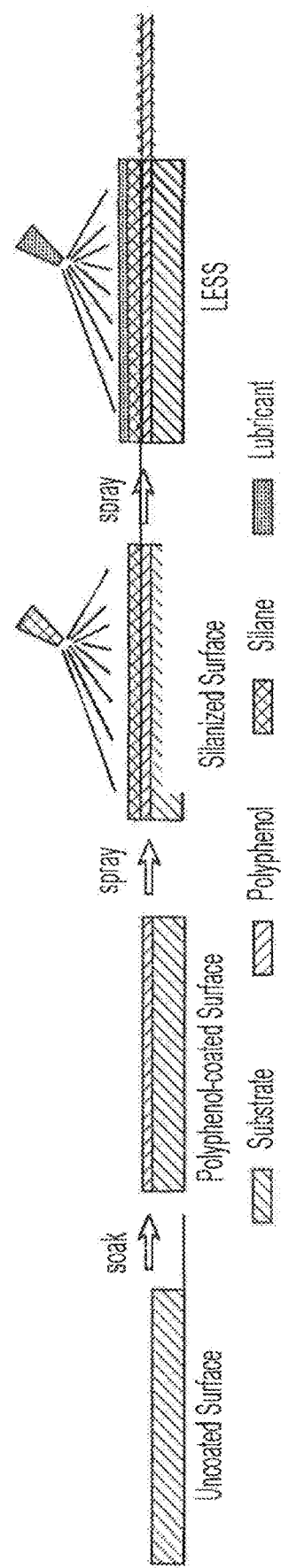
FIG. 1a illustrates a process of coating a substrate to form a slippery surface thereon in accordance with an aspect of the present disclosure.

In developing a slippery surface on plastics, it was found that using conventional approaches, such as attempting to functionalize the surface of plastics by an oxygen plasma process followed by silanization, that the plastic surfaces could not be readily silanized or were difficult to silanize. However, it was found that by forming a polyphenol layer on the surface of plastic materials followed by silanization and formation of a lubricant layer thereover, slippery surfaces could readily be prepared. It was also found that such a process could be applied to a variety of materials.

Accordingly, the present disclosure relates to substrates having slippery surfaces that can repel various liquids and viscoelastic solids with anti-biofouling properties by first forming a polyphenol layer on the substrate's surface followed by forming a silanization layer directly on the polyphenol layer, and a lubricant over the silanization layer. Slippery surfaces according to the present disclosure can be formed on a variety of materials such as polymers, metals, ceramics, glasses, or combinations thereof. In particular, the slippery surfaces according to the present invention can be formed on industrial and medical materials that can be challenging to chemically functionalized such as polymeric substrate materials. In addition, slippery surfaces according to the present disclosure can advantageously be formed under ambient conditions (i.e., in air under atmospheric pressures and ambient temperatures) and with liquid-phase processing thereby avoiding complex equipment and processing conditions.

In one aspect of the present disclosure, a surface of a substrate has a slippery surface. The slippery surface includes a layer of polyphenol on the surface of the substrate, a silanization layer directly on the polyphenol layer, and a lubricant over the silanization layer. Slippery surfaces can be formed on a variety of substrate materials including polymers (e.g. polystyrene, polyvinyl chloride, polyethylene, polypropylene, polycarbonate, silicone, rubber, etc.), semiconductors, e.g., silicon, metals (e.g., titanium, steel, aluminum, etc.), ceramics, glass, etc., or combinations thereof. Advantageously, the slippery surface according to the present disclosure can be readily formed over a large area of the substrate surface such as no less than about 50 $cm^2$, 100 $cm^2$, 200 $cm^2$, and greater than about 500 $cm^2$.

In practicing certain aspects of the present disclosure, it is preferable to form the slippery surface on a substrate with a relatively smooth surface. In some embodiments, the substrate surface has an average roughness ($R_a$) at a microscale level, e.g., $R_a$ of less than a few microns, and preferably less than a few hundred nanometers, or even less than a few nanometers. Advantageously, the surface of the substrate to be coated is relatively smooth, e.g., the surface has an average roughness $R_a$ of less than about 4 µm, e.g., less than about 2 µm and less than about 1 µm average surface roughness and even less than about 500 nm, e.g., less than about 100 nm average surface roughness. An advantage of the slippery surface coating of the present disclosure is that the underlying surface substrate is not roughened prior to depositing the coating on the surface.

It was found that an effective slippery surface can be formed on a substrate by first forming a polyphenol layer on the surface. A polyphenol (also known as a polyhydroxyphenol) as used herein refers to a compound with at least three phenol groups in which each phenol group has one or more exposed hydroxyl groups. Preferably, polyphenols formed on the surface of the substrate have more than three phenol groups with each phenol having at least one exposed hydroxyl groups. Example of polyphenols useful in preparing slippery surfaces include plant-derived polyphenols such as tannic acid, epigallocatechin gallate, epicatechin gallate, epigallocatechin, raspberry ellagitannin, theaflavin-3-gallate, tellimagrandin II, etc. or combinations thereof. In addition, a polyphenol layer can be formed on a surface of a substrate by reacting several phenols of the same or different types with or without other reactants on the substrate surface. For example, such a polyphenol layer can be formed by reacting one or more of a phenol such as a catechol, caffeic acid, ferulic acid, gallic acid, pyrogallol, phenylpropanoid-derived gallic acid, epigallocatechin gallate, epicatechin gallate, epigallocatechin, a catechol amine such as dopamine, etc.

A polyphenol layer can be formed on the substrate surface by dipping or coating the substrate in or with a solution or mixture including a polyphenol and removing the solution or liquid medium to leave the polyphenol layer on the substrate surface. Alternatively, a polyphenol layer can be formed on the substrate surface by applying a solution or mixture of one or more phenols with a catalyst, such as a base or acid, to react the phenols to form a polyphenol layer on the surface of the substrate.

In some embodiments, the polyphenol layer can be formed with a thickness at a sub-nanometer height, e.g., less than about 100 nm, such as less than about 50 nm, e.g., less than about 7 nm and even less than about 5 nm. In other embodiments, the polyphenol can be formed with a thickness in a range of from about 2 nm to about 20 nm, e.g., between about 3 nm and about 10 nm. Advantageously, the polyphenol layer can be formed on the substrate surface by contacting the substrate with a solution including the polyphenol or with a solution including phenol to form the polyphenol layer.

It is believed that the polyphenol layer readily adheres to surfaces by static and hydrogen bonding as well as π-π stacking thereby providing a hydroxyl functionalized surface for subsequently anchoring a silanization layer. Hence by a simple technique of forming a polyphenol layer on to a surface of a surface, we were able to introduce a plurality of hydroxyl groups adhered to the surface of the substrate, which can be used for additional chemistry on the surface.

A silanization layer can then be directly formed on the polyphenol layer. A silanization layer herein refers to an array of silanes and/or siloxanes or combinations thereof anchored to the polyphenol layer. The anchored silanes and/or siloxanes can have an alkyl group and long alkyl chains, e.g., alkyl group of $C_{1-30}$, such as alkyl chains of $C_{6-30}$, which can be substituted with fluoro- and perfluorinated groups. In some embodiments, the array of silane and/or siloxanes or combinations thereof are an array of linear (i.e., straight-chain) polysilanes or polysiloxanes or a combination thereof having ends anchored to the polyphenol layer and opposite ends extending away from the polyphenol layer. The silanization layer can be anchored to the polyphenol layer by chemical covalent bonds which can be formed by reacting the silanization chemicals with the hydroxyls on the polyphenol layer.

The silanization layer can be formed directly on polyphenol layer by reacting a silane or siloxane with exposed hydroxyl groups on the polyphenol layer. For example, the silanization layer can be formed from by reacting exposed hydroxyl groups on the polyphenol layer with one or more of an alkoxysilane such as a mono-alkoxy silane, e.g., trimethylmethoxysilane, a di-alkoxy silane, e.g., di-alkoxy, dialkyl silane, e.g., dimethyldimethoxysilane, a di-alkoxy, diphenyl silane, a di-alkoxy, floroalkyl or perfluorosilane, a tri-alkoxy silane, e.g., 1H,1H,2H,2H-perfluorodecyltriethoxysilane, a siloxane, such as hexamethyldisiloxane, a cyclic siloxane, e.g., octamethylcyclotetrasiloxane, an alkyl, a chlorosilane, e.g., octyldimethylchlorosilane etc. The alkoxy groups of such silanes and siloxanes can be $C_{1-4}$ alkoxy groups such as methoxy (—$OCH_3$), ethoxy (—$OCH_2CH_3$) groups and the alkyl groups can have various chain lengths, e.g., alkyl groups of $C_{1-30}$. In addition, the silanization layer can be formed directly on the polyphenol layer by polymerizing one or more a silane or siloxane from exposed hydroxyl groups on the polyphenol layer to form an array of linear polysilanes or polysiloxanes or a combination thereof. By this technique, the array of linear polymers has ends anchored to the polyphenol layer and opposite ends extending away from the polyphenol layer and resemble a brush or comb. Such an array of linear polysilanes or polysiloxanes or a combination thereof can be polymerized from a solution applied to the polyphenol layer on the substrate followed by drying, wherein the solution includes: (i) a polymerizable silane or siloxane, or combination thereof, (ii) a solvent, e.g., an aqueous solvent, and (iii) an acid catalyst. Useful solvents include alcohols such as ethanol, isopropanol, ketones such as acetone, methylethylketone, chlorinated solvents such as chloroform, etc. Water can also be used as a co-solvent. Useful acid catalysts include sulfuric acid, hydrochloric acid, acetic acid, nitric acid etc. A silanization layer formed by a linear array of polysilanes or polysiloxanes or a combination thereof advantageously can be prepared by coating and drying a polysilane and/or polysiloxane on to a layer of polyphenol on a substrate surface in air at atmospheric pressure and at temperatures from about from 0° C. to 60° C., and relative humidity from 30% to 80% in a period of less than 120 minutes, e.g., less than 60 minutes and even as short as in less than 30 minutes. In one embodiment of the present disclosure, the silanization layer is an array of linear polydimethylsiloxanes and/or perfluorosilane grafted on the polyphenol layer.

Silanization chemicals can be applied to the surface substrate having a polyphenol layer by simply submerging the substrate (dip-coating) or coating the silanization chemicals on to the substrate such as by spraying or spin coating the silanization chemicals on the substrate to form the silanization layer directly on the polyphenol layer. Certain silanization layers can also be formed by chemical vapor deposition (CVD) techniques but such techniques require relatively more complex equipment and generally require a vacuum rather than atmospheric pressures.

In some embodiments, the silanization layer can be formed to have a thickness at a sub-nanometer height, e.g., less than about 50 nm, such as less than about 20 nm, e.g., less than about 7 nm and even less than about 5 nm. In other embodiments, the silanization layer can be formed with a thickness in a range of from about 2 nm to about 20 nm, e.g., between about 3 nm and about 10 nm. Advantageously, the silanization layer can be formed directly on the polyphenol layer by a contacting the substrate having the polyphenol layer.

A lubricant layer can then be formed over the silanization layer. Preferable, the lubricant is chosen to have a strong chemical affinity to the silanization layer or substrate so that the lubricant can fully wet and stably adhere on the surface. A stable lubricant layer over the silanization layer would be entrenched in the silanization layer, i.e., the lubricant layer would be over and within the silanization layer and adhere to the silanization layer. Forming a stable lubricant layer over the silanized layer results in a surface with anti-biofouling properties and that repel various liquids and viscoelastic solids.

In some embodiments, the lubricant can be one or more of an omniphobic lubricant, a hydrophobic lubricant and/or a hydrophilic lubricant. The lubricant can include a perfluorinated oil or a silicone oil or a hydroxy polydimethylsiloxane (PDMS) or a plant oil. Preferable, the lubricant is chosen to have a strong chemical affinity to the silanization layer or substrate so that the lubricant can fully wet and stably adhere on the surface. For example, perfluorinated oils (e.g., Krytox oil) can form a stable lubrication layer over a silanization layer including fluorinated silanes such as perfluorinated silanes. Silicone oil can form a stable lubricant layer over a silanization layer including siloxanes such as a linear array of polydimethylsiloxane (PDMS), for example. Hydroxy PDMS can also form a stable lubricant layer over a silanization layer including siloxanes such as a linear array of polydimethylsiloxane (PDMS), for example. Mineral oils can form a stable lubricant layer over a silanization layer including alkyl silanes which can be formed by depositing alkyltrichlorosilanes or alkyltrimethoxysilanes on the polyphenol layer. The alkyl groups on such alkylsilanes can have various chain lengths, e.g., alkyl chains of $C_{1-30}$. Other lubricants that will be compatible with alkylsilanes or siloxanes with various chain lengths include alkane oils (e.g. decane, dodecane, hexadecane, or a mixture of them etc.), olive oil, palm oil, soybean oil, canola oil, rapeseed oil, corn oil, peanut oil, coconut oil, cottonseed oil, palm oil, safflower oil, sesame oil, sunflower oil, almond oil, cashew oil, hazelnut oil, macadamia oil, Mongongo nut oil, pecan oil, pine nut oil, walnut oil, grapefruit seed oil, lemon oil, orange oil, amaranth oil, apple seed oil, argan oil, avocado oil, babassu oil, ben oil, borneo tallow nut oil, cape chestnut oil, carob pod oil, coca butter, cocklebur oil, cohune oil, grape seed oil, Kapok seed oil, Kenaf seed oil, Lallemantia oil, Manila oil, Meadowfoam seed oil, mustard oil, Okra seed oil, papaya seed oil, Pequi oil, poppyseed oil, pracaxi oil, prune kernel oil, quinoa oil, ramtil oil, Sapote oil, Shea butter, tea seed oil, tigernut oil, tomato seed oil, and other similar plant-based oils etc. The plant-based oils can be used alone or with other lubricants or as a mixture of plant-based oils alone or with other lubricants. Lubricant viscosities ranging from ~1 cSt to ~1000 cSt as measured at 25° C., such as from 2 cSt, 3 cSt, 4 cSt, 5 cSt, to 1000 cSt as measured at 25° C., would be preferable.

The slippery surfaces of the present disclosure can be prepared by a facile fabrication process. FIG. 1a illustrates a process of coating a substrate to form a slippery surface thereon in accordance with an aspect of the present disclosure. For this example, a smooth substrate (e.g., a substrate with a surface having an average roughness of less than 1 μm) was immersed into a polyphenol solution and soaked for about 0.5 hr to about 2 hr. Then the substrate was sprayed with a silane coating solution, and dried in air for 5-10 min. A lubricant layer was then spray coated onto the coated substrate.

Figure 1B:
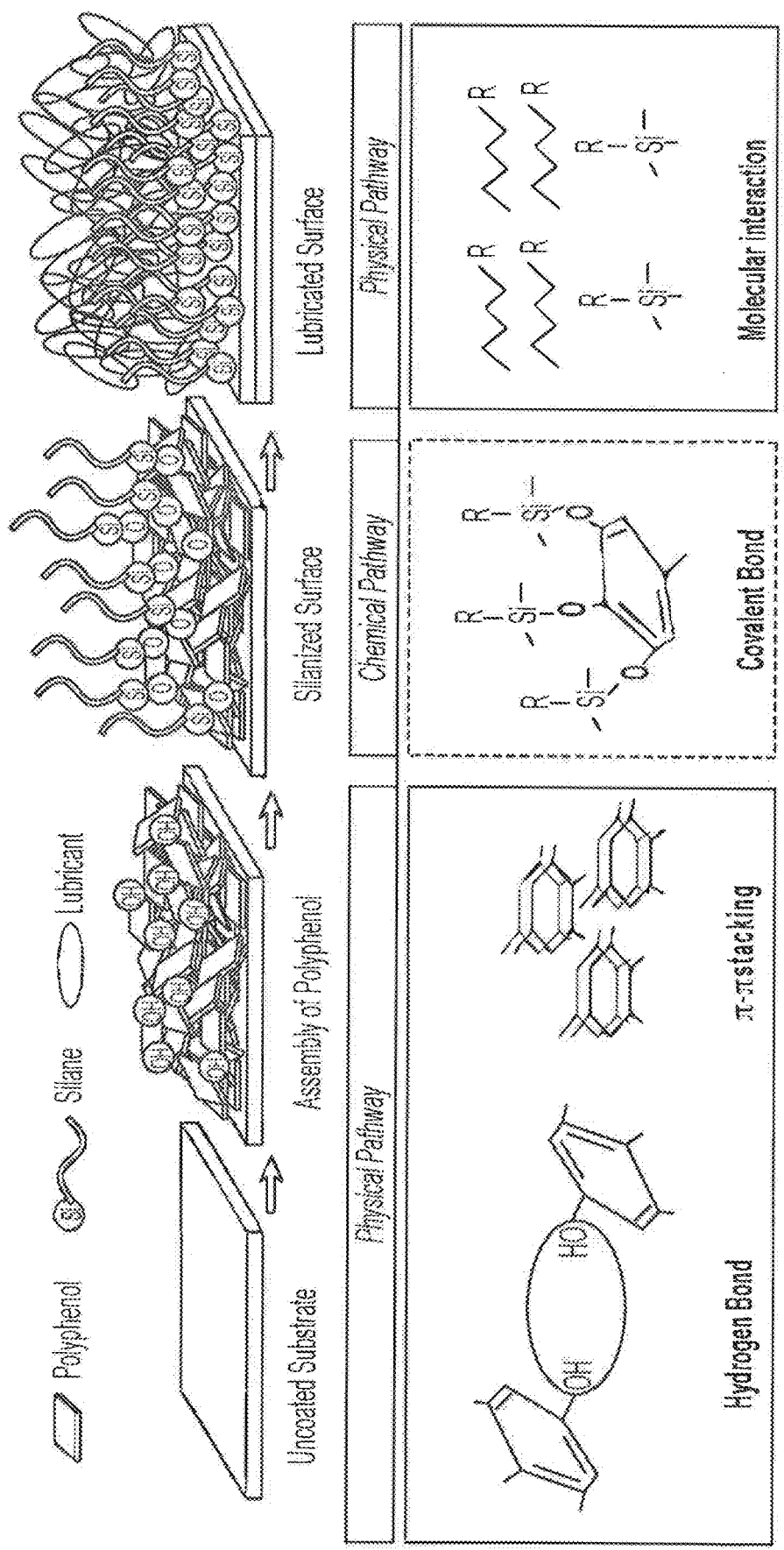
FIG. 1b illustrates a process of coating a substrate to form a slippery surface thereon as the process is believed to occur at a molecular scale in accordance with an aspect of the present disclosure.
Figure 4:
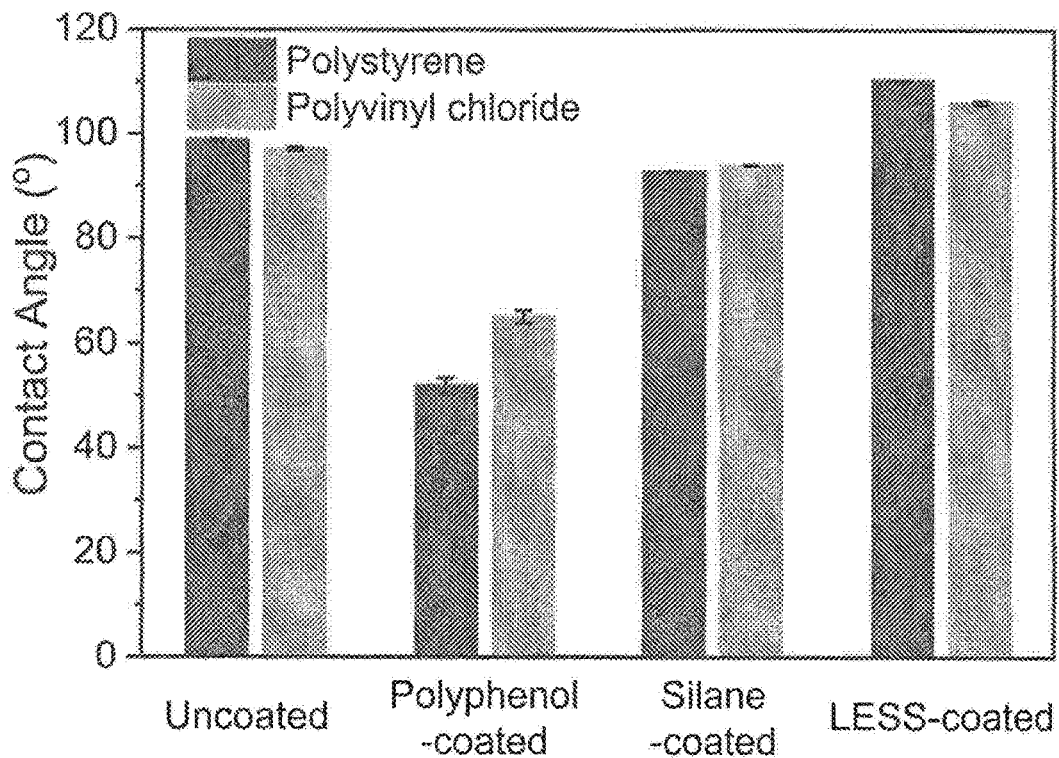
FIG. 4 shows the contact angle (CA) of water on polystyrene and polyvinyl chloride (PVC) sheets before and after various treatment of the surface of the sheets.

To further illustrate the coating process as it is believed to occur on a molecular scale, FIG. 1b shows how a polyphenol layer can adhere on a substrate and how the polyphenol can adhere to each other through either hydrogen bonding or π-π stacking or both. Thus, it is believed that the polyphenol layer adheres to the substrate surface by a physical adhesion through intermolecular forces (e.g., van der Waals interaction). After, applying a silane or siloxane, the silane or siloxane reacts with the hydroxyl groups in polyphenol molecules forming a covalent bond to the polyphenol layer. As depicted in the figure, the silanization layer has an array of chains with ends anchored to the polyphenol layer and opposite ends extending away from the polyphenol layer. The silanization layer can be attached to the polyphenol layer by either condensation polymerization of monomers or through direct attachment of linear polymers. Then with applying a stable lubricant, the molecules of lubricant have strong chemical affinity (similar chemistry with silane or siloxane) to the silanized layer, which is also a physical adhesion.

For experimentation, smooth polystyrene (PS) sheets were cleaned by ethanol and then coated with tannic acid via a tannic acid coating solution under atmospheric pressure and temperature. For example, a tannic acid layer can be coated on the surface of a substrate by soaking the substrate for 2-hours in a mildly alkaline, saline solution (e.g., pH ~8) including 2 mg/mL tannic acid under atmospheric pressure and temperature. Alternatively, a tannic acid layer can be coated on the surface of a substrate by using a solution of 2 mg/mL tannic acid in DI water under atmospheric pressure and temperature. After the soaking process, the surfaces were rinsed with deionized water, and dried under a nitrogen flow. It was observed that the polyphenol layer formed by this process strongly adhered on the substrate surface. It was also observed that the surface character changed from a hydrophobic to a hydrophilic character after the substrate was soaked in the polyphenol solution (See FIGS. 2a-2b and FIGS. 3a-3b). With the tannic acid layer on the substrate, the surfaces were sprayed with 1H,1H,2H,2H-perfluorodecyltriethoxysilane solution and dried in ambient condition, e.g., under air at atmospheric pressure and temperature. After rinsing with isopropanol, the polystyrene sheets included a polyphenol layer on the surface and a silanization layer directly on the polyphenol layer. The surfaces became hydrophobic again (FIGS. 2c and 3c). It should be noted that the combined polyphenol layer and silanization layer can be formed such that they do not introduce any significant additional roughness to the substrate surface. Further, when the silanization chemicals are soluble in the lubricant applied in the subsequent step, the rinsing process can be skipped as the excess silanization chemical would be soluble in the lubricant. To complete forming a slippery surface, e.g., a liquid lubricant-entrenched smooth surface (LESS), lubricant (e.g. Krytox 100, a perfluorinated lubricant) was applied onto the silanization layer by spin or spray coating. This process formed a stable, completely wetted lubricant layer over and within the silanization layer since the lubricant and silanization layer are substantially compatible. With such a slippery surface on the substrate, the surfaces can completely repel water (FIGS. 2d and 3d) and any other aqueous based liquid, e.g., immiscible liquids.

Contact angles were measured on polystyrene after each coating step to illustrate the successful formation of various chemical layers. FIGS. 3a-3d and FIG. 4 demonstrate the surface hydrophobicity change from uncoated polystyrene to the LESS-coated one. The polymer surface was hydrophobic before the first polyphenol coating and was hydrophilic after the first coating. The hydrophobicity was restored by applying the second chemical layer and the lubricant as well. The contact angle of a 10 μL water drop on uncoated smooth polystyrene is 98.7°±0.2°. After coated with tannic acid, the contact angle changed to 51.8°±1.5°. With a fluorosilane coating, the surface restores its hydrophobicity with a contact angle of 92.7°±0.2°. Finally, the LESS-coated polystyrene has a contact angle of 110.2°±0.1°. The contact angle changes with each coating step similarly on polyvinyl chloride (PVC).

Figure 5:
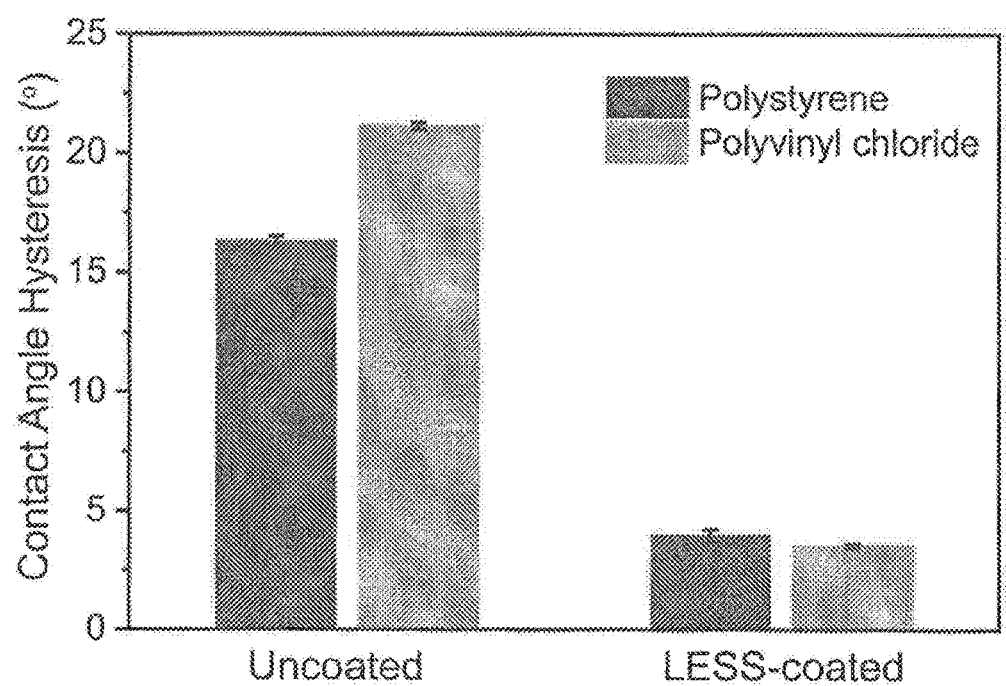
FIG. 5 shows a comparison between contact angle hysteresis (CAH) of water on polystyrene and polyvinyl chloride treated as shown in FIG. 4.

To demonstrate the slipperiness of the treated surface, we measured the contact angle hysteresis (CAH) on uncoated and the LESS-coated surfaces of polystyrene (PS) and polyvinyl chloride (PVC), shown in FIG. 5. The CAH is 16.3±0.2 and 21.1±0.2 for uncoated PS and PVC, respectively. With a liquid lubricant-entrenched smooth surfaces coating, the CAH is 4.0±0.3 and 3.5±0.1 for PS and PVC, respectively. The contact angle hysteresis of water on polymers drops from ~20° to less than 5°.

Figure 6:
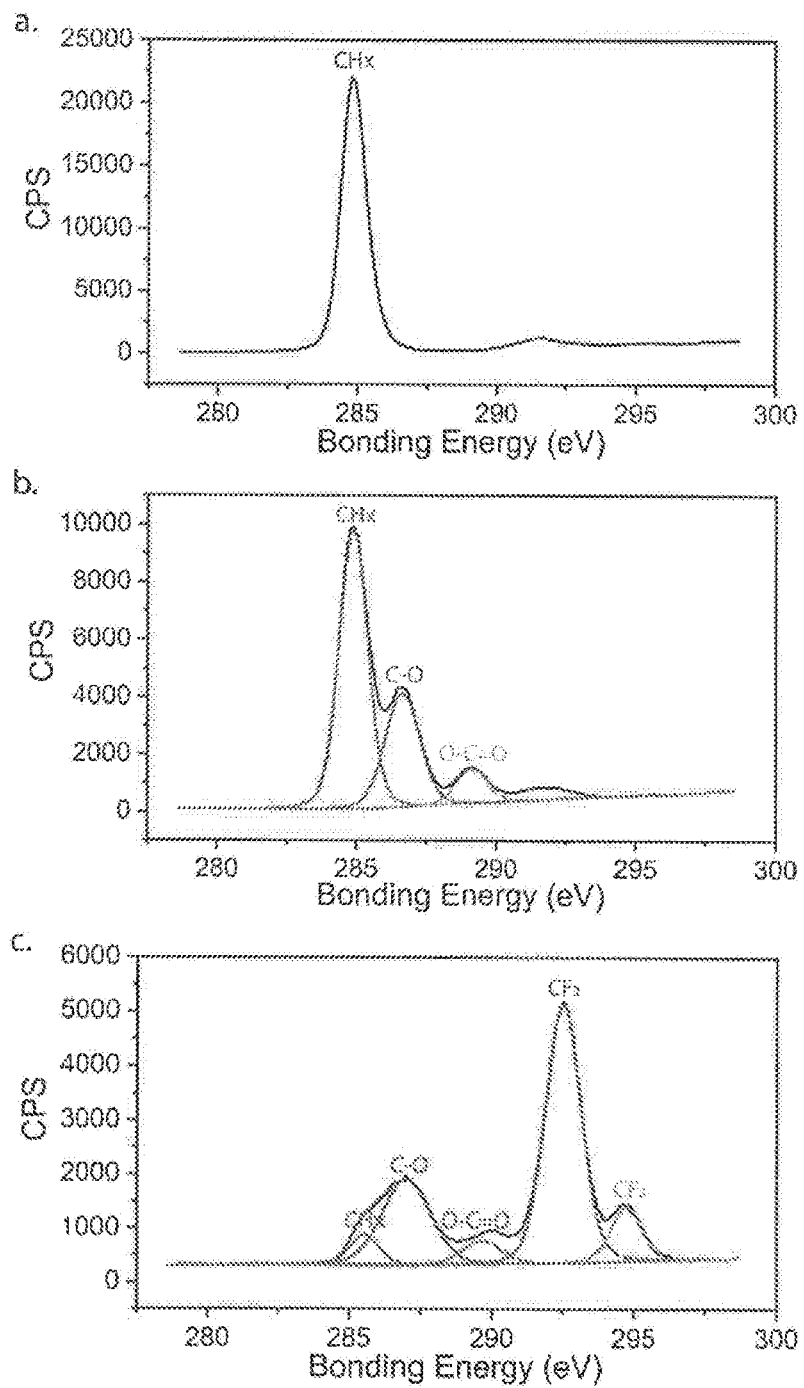
FIGS. 6a-6c show XPS data (C1 s3) of different surfaces, including polystyrene, tannic acid adhered polystyrene, and tannic acid adhered polystyrene after silanization.

The existence of the tannic acid layer and the perfluorinated silane layer were further shown with X-ray photoelectron spectroscopy (XPS) measurement. In FIG. 6a, the C 1s spectrum of the polystyrene sample contained strong CHx and aromatic bands indicative a polystyrene. The tannic acid treated sample showed features consistent with tannic acid, shown in FIG. 6b. These included large C—O and O—C=O bands in the C 1s and O 1s spectra. Assuming a uniform overlayer model the thickness of the tannic acid layer is estimated to be ~3 nm. The tannic acid adhered polystyrene after silanization contained $CF_2$, $CF_3$ and silicon, all are consistent with perfluorodecyl silane, shown in FIG. 6c. A significant C—O band was still evident in the C 1s spectrum. This is consistent with a buried tannic acid layer under the silane. Using the relative amount of $CF_2$ or the total F, the fluorosilane layer is estimated to be —3 nm. Based on our XPS measurements, there are a combined ~6 nm layer of tannic acid and silane covering the substrate.

Figure 7:
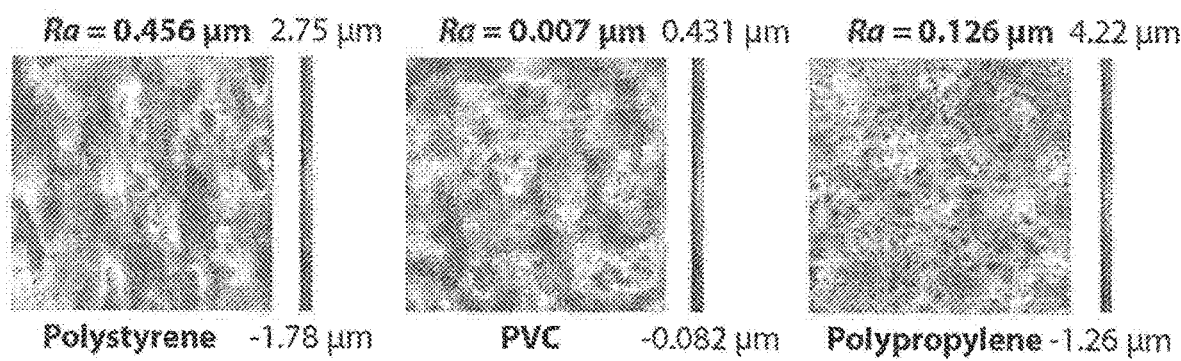
FIG. 7 shows images of surface roughness of polystyrene, polyvinyl chloride, and polypropylene.
Figure 8:
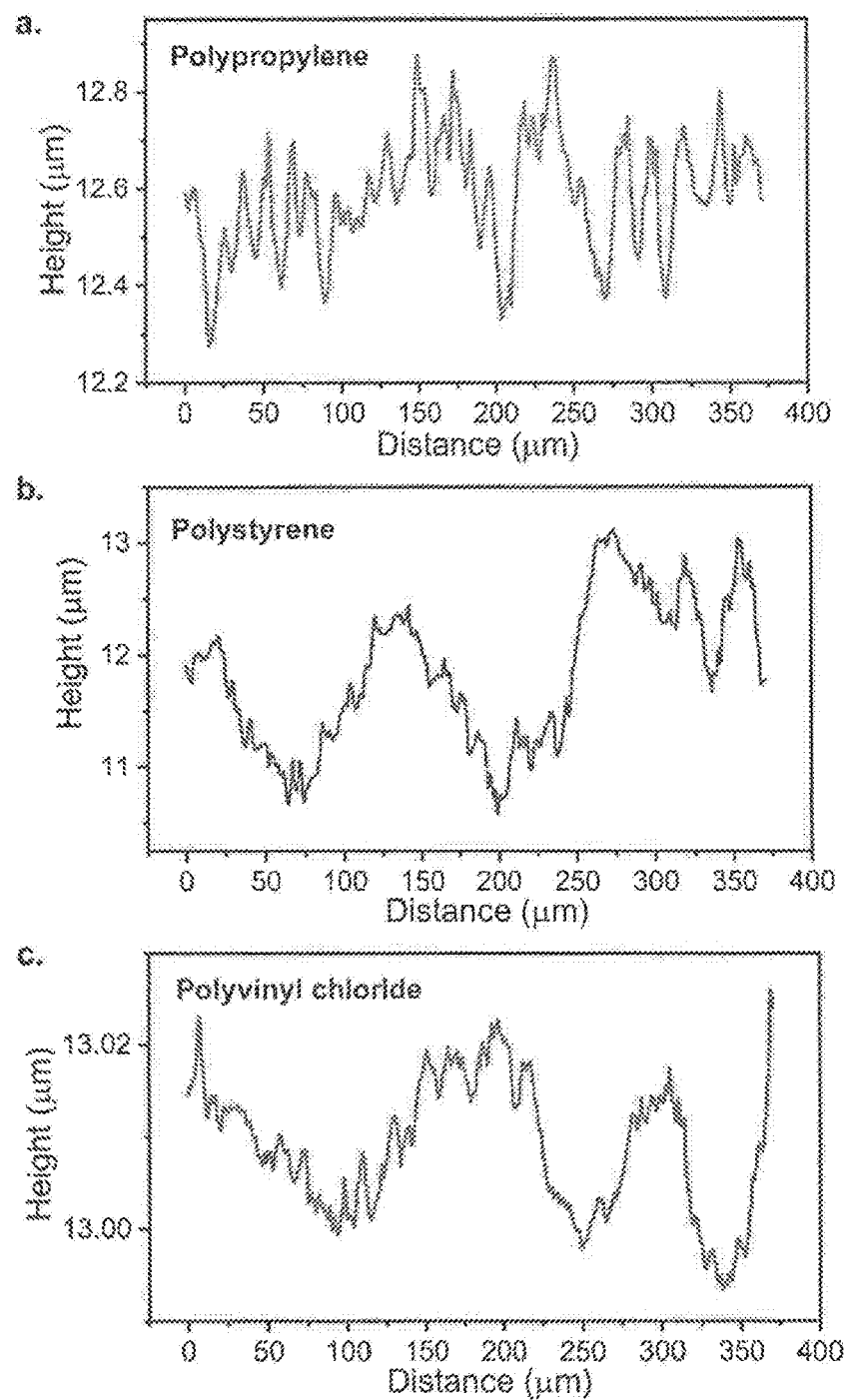
FIGS. 8a-8c illustrate the surface profile of polystyrene, polyvinyl chloride, and polypropylene.

Different from traditional SLIPS, these liquid lubricant-entrenched smooth surfaces of the present disclosure do not require surface roughness to retain lubricant. The presence of the surface roughness in traditional SLIPS may lead to enhanced adhesion of the viscoelastic solids or other biological waste upon impact. In certain embodiments, the surface roughness does not need to be altered prior to applying a coating according to the present disclosure. In other embodiments, the surface can be smoothened, not roughened, prior to applying a coating according to the present disclosure. The surface roughness was measured to show the smoothness of various substrates used as obtained from commercial sources. As shown in FIG. 7, the measured area is 0.475 mm×0.475 mm. The polymeric surfaces used for creating liquid lubricant-entrenched smooth surfaces have an average surface roughness $R_a$ of less than 1 μm. The roughness ($R_a$) is 0.456 μm, 0.007 μm, 0.126 μm for polystyrene, polyvinyl chloride, and polypropylene, respectively. The smoothness of the substrate is confirmed with the surface roughness profile, as shown in FIGS. 8a-8c. All roughness and profile measurement were measured by Zygo optical profilometer.

Figure 9:
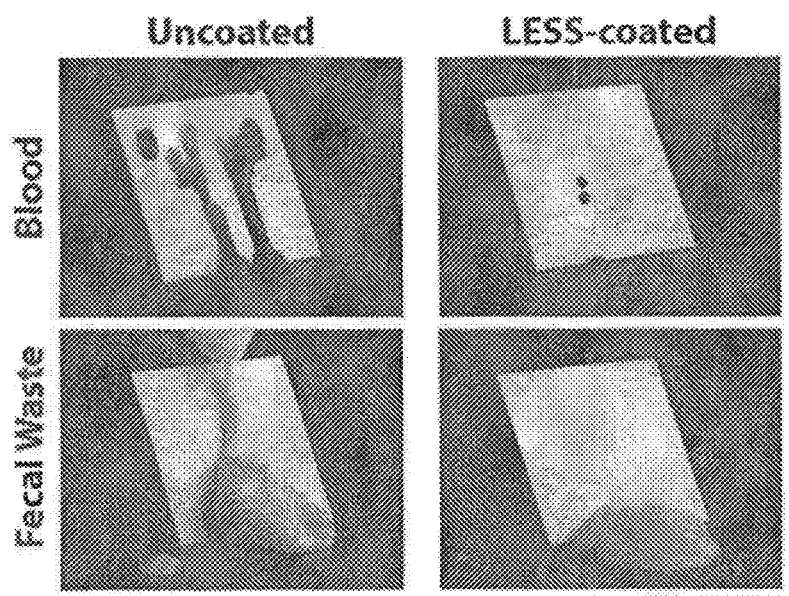
FIG. 9 shows images comparing blood and synthetic feces repellency between uncoated and a slippery surface of polystyrene prepared according to an aspect of the present disclosure, e.g., a liquid lubricant-entrenched smooth surface (LESS)

The repellency of the LESS-coated surfaces to blood (biological complex fluid) and feces (viscoelastic solid) were also demonstrated. From FIG. 9, uncoated polystyrene can be easily contaminated with sheep blood and adhered with synthetic feces. However, a LESS-coated polystyrene can remain clean after being impacted with both blood and feces, as shown in FIG. 9. Both sheep blood and synthetic feces stick to the uncoated surface but are repelled by LESS treated surface.

Figure 10:
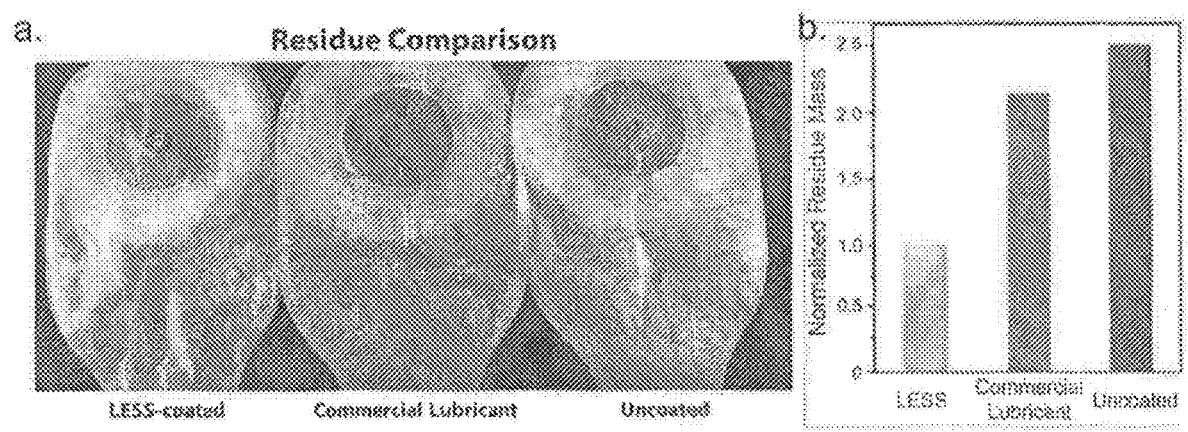
FIGS. 10a-10b show a comparison on synthetic feces residue performance in ostomy bags among uncoated, a commercial lubricant, and LESS coated bag.

With the demonstration of repelling synthetic feces, an ostomy bag was treated to form another slippery surface according to the present disclosure, e.g., another liquid lubricant-entrenched smooth surface. The ostomy bag used for this experiment was a ConvaTec ActiveLife One-Piece Cut-to-Fit Transparent Drainable Pouch with Stomahesive Skin Barrier (#22771). The pouch combines the skin barrier and the pouch in one system, where the pouch allows for draining of human waste and the skin barrier helps to protect the skin against semi-formed to formed stool. The ostomy bag is a drainable pouch designed to be opened at the bottom when emptying. The ostomy bag can comprise a front and rear wall made of flexible plastic films such as one or more layers of ethylene vinyl acetate (EVA) and one or more layers of a gas barrier material such as poly(vinylidene chloride) (PVDC). See, e.g., U.S. Pat. Nos. 8,343,121, 9,707,120, and 10,105,255. The slippery surface was formed on internal surfaces of the ostomy bag. The slippery surface including a polyphenol layer prepared by tannic acid and a silanization layer directly on the polyphenol layer prepared by polymerizing dimethyldimethoxysilane directly on the polyphenol layer followed by forming a lubricant layer over the silanization layer by silicone oil. Specifically, the polyphenol layer was prepared by soaking in the tannic acid aqueous solution (2 g/L) overnight and ambient drying for 1~2 hours, and the silanization layer on the polyphenol layer was prepared by polymerizing dimethyldimethoxysilane directly on the polyphenol layer through the condensation polymerization process. This polymerization process of dimethyldimethoxysilane was prepared by soaking in the silane solution (10 wt % dimethyldimethoxysilane, 1 wt % sulfuric acid, and 89 wt % isopropanol) for 10~20 second and ambient drying for 30 min to 1 hour. Finally, a conformal and stable lubricant layer was applied by wiping or spraying over the silanization layer as silicone oil (25 cSt). To demonstrate the effectiveness of a slippery surface prepared according to the present disclosure, 100 grams of synthetic feces (20% solid content) were put into the bag and then squeezed out of the ostomy bag. From the images shown in FIGS. 10a-10b, the LESS-coated bag left the least amount of residues (5.10 g) compared to an uncoated bag (13.13 g) and a commercially lubricated bag (11.16 g). Overall, the LESS-coated bag can lead to greater than 100% less residue than those of the uncoated bag and the one coated with a commercially available lubricant. From the image and the plot in FIGS. 10a-10b, the LESS treated bag resulted in retaining the least of the feces residue. The residue masses in all of the ostomy bags shown in the plot are normalized by the residue mass in the LESS-coated ostomy bag.

The LESS-coated substrates can also reduce adhesion to a range of pathogens and Gram-positive and Gram-negative bacteria by over 99% as compared to untreated substrates. These pathogens include but not limited to *Staphylococcus aureus, Enterobacter cloacae, Escherichia vulneris, Escherichia hermannii, Acinetobacter calcoaceticus, Enterococcus mundtii*, and *Escherichia coli*.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Fabrication Process of Liquid lubricant-Entrenched Smooth Surfaces

The polyphenol layer was formed by a soaking process. Hydroxyl groups are successfully created on the substrate with this layer. As a demonstration, tannic acid was used to form the polyphenol layer directly on a surface of a smooth substrate. Tannic acid was used at a concentration of 2 mg/mL in deionized water to form the polyphenol layer directly on various substrate surfaces including on polystyrene, polyvinyl chloride, and polypropylene. The coating process alternatively can be carried out under a mildly alkaline, saline solution (e.g., pH ~8) by the addition of sodium chloride and tris(hydroxymethyl)aminomethane (or Tris), under atmospheric and ambient conditions. The substrates were submerged into the tannic acid solution for more than 2 hours, followed by drying in room conditions (20° C., 1 atm) for 5 min.

After forming the polyphenol layer on the surface of the substrate, a silanization layer was covalently bonded to the polyphenol layer by reacting an alkoxy, alkyl silane thereto. As a demonstration, (1H,1H,2H,2H-Perfluorodec-1-yl)tris(ethoxy)silane was used to form the silanization layer. A silane solution including 10 wt % (1H,1H,2H,2H-Perfluorodec-1-yl)tris(ethoxy)silane in 89 wt % isopropanol with 1 wt % of sulfuric acid was spray coated onto the substrate surface having the polyphenol layer thereon. The substrates with polyphenol layer was sprayed with the silane solution and dried in air under atmospheric pressure for less than 10 min.

Another example of the silane solution included a mixture of 10 wt % of alkyltrichlorosilane, 1 wt % of sulfuric acid, 89 wt % of isopropanol. Yet another example of the silane solution included a mixture of 10 wt % of alkyltrichlorosilane, 1 wt % of hydrochloric acid, 89 wt % of isopropanol. The substrates with polyphenol layer can be sprayed with the silane solution and dried in air under atmospheric pressure for less than 10 min.

Another example of the silane solution included a mixture of 10 wt % of dimethyldimethoxysilane, 1 wt % of sulfuric acid, 89 wt % of isopropanol. Yet another example of the silane solution included a mixture of 10 wt % of dimethyldimethoxysilane, 1 wt % of hydrochloric acid, 89 wt % of isopropanol. This example of silane solution forms a linear chain of grafted polymer brush onto a surface through condensation polymerization of monomers. The substrates with polyphenol layer can be sprayed with the silane solution and dried in air under atmospheric pressure for less than 10 min.

After the silanization process formed by perfluorinated silanes, the surfaces were lubricated by a perfluorinated lubricant, such as Krytox 101 and other Krytox lubricants.

For the silanization process formed by dimethyldimethoxysilane, the surface can be lubricated by silicone oil, hydroxy polydimethylsiloxane, a plant oil, or a mineral oil.

For the silanization process formed by an alkyltrichlorosilane, the surface can be lubricated by a plant oil or mineral oil.

Contact Angle and Contact Angle Hysteresis Measurement

The contact angle of a 10 μL water drop on different surfaces was measured with ramé-hart goniometer with an angle measurement resolution of 0.1°. The contact angle hysteresis was calculated by the subtraction of advancing and receding angle. The advancing and receding angles were measured by tilting the surface with a 10 μL water drop.

XPS Measurement

XPS experiments were performed using a Physical Electronics VersaProbe II instrument equipped with a monochromatic Al kα x-ray source (hv=1,486.7 eV) and a concentric hemispherical analyzer. Charge neutralization was performed using both low energy electrons (<5 eV) and argon ions. The binding energy axis was calibrated using sputter cleaned Cu (Cu $2p_{3/2}$=932.62 eV, Cu $3p_{3/2}$=75.1 eV) and Au foils (Au $4f_{7/2}$=83.96 eV). Peaks were charge referenced to $CH_x$ band in the carbon 1s spectra at 284.8 eV. For the perfluorosilane sample, charge correction was done by assuming the $CF_2$ band was at 292.5 eV. Measurements were made at a takeoff angle of 45° with respect to the sample surface plane. This resulted in a typical sampling depth of 3-6 nm (95% of the signal originated from this depth or shallower). Quantification was done using instrumental relative sensitivity factors (RSFs) that account for the x-ray cross section and inelastic mean free path of the electrons.

Surface Roughness Measurement

Surface roughness of different substrates was measured by Zygo optical profilometer. The measured area was 475× 475 μm².

COMPARATIVE EXAMPLE

Polystyrene as substrate was used for control experiment. In this experiment, no polyphenol layer was applied to the polystyrene sheet but the sheet was otherwise prepared as described above for Fabrication Process of Liquid lubricant-Entrenched Smooth Surfaces. That is, a polystyrene sheet was sprayed with the same silane solution described above for Fabrication Process of Liquid lubricant-Entrenched Smooth Surfaces and dried in air for 10 min. Then Krytox 101 was sprayed onto the treated surface. Continuous water drops were sprayed onto the lubricated surface. After less than about 10 drops, water drops stuck to the substrate and could not be repelled anymore. In contrast, a LESS surface as described above for Fabrication Process of Liquid lubricant-Entrenched Smooth Surfaces can typically repel continuous water drops sprayed onto the lubricated surface in excess of about 100,000 drops.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A substrate having a surface, the surface being an untreated surface, the substrate comprising:
    a layer of polyphenol formed on the surface;
    a silanization layer formed directly on the polyphenol layer, the silanization layer comprising an array of straight-chain polysiloxanes having ends anchored to the polyphenol layer and opposite ends extending away from the polyphenol layer; and
    a lubricant disposed over the silanization layer.

2. The substrate of claim 1, wherein the surface of the substrate before forming the layer of polyphenol and layer of salinization has an average roughness of less than 1 µm.

3. The substrate of claim 1, wherein the silanization layer has a thickness of from about 2 nm to about 20 nm.

4. The substrate of claim 1, wherein the lubricant comprises one or more of an omniphobic lubricant, a hydrophobic lubricant and/or a hydrophilic lubricant.

5. The substrate of claim 1, wherein the lubricant comprises one or more of silicone oils or mineral oils.

6. The substrate of claim 1, wherein the surface comprises a polystyrene, polyvinyl chloride, polyethylene, polypropylene, polycarbonate, silicone, rubber, ethylene vinyl acetate, poly(vinylidene chloride) or combinations thereof.

7. The substrate of claim 1, wherein the silanization layer comprises an array of linear polysiloxanes polymerized from a di-alkoxy silane in a solution which is applied to the polyphenol layer.

8. The substrate of claim 1, wherein the polyphenol layer comprises a catechol amine.

9. The substrate of claim 1, wherein the polyphenol comprises a tannic acid, epigallocatechin gallate, epicatechin gallate, epigallocatechin, raspberry ellagitannin, theaflavin-3-gallate, tellimagrandin II, or combinations thereof.

10. The substrate of claim 1, wherein the polyphenol layer has a thickness of less than about 100 nm.

11. The substrate of claim 1, wherein the surface comprises a polymer.

12. The substrate of claim 1, wherein the surface comprises a metal, ceramic, glass or a combination thereof.

13. The substrate of claim 1, wherein the substrate comprises a medical device having a polymeric surface.

14. The substrate of claim 1, wherein the substrate comprises an ostomy bag having a polymeric surface.

15. The substrate of claim 1, wherein the substrate comprises a catheter.

16. The substrate of claim 1, wherein the substrate comprises a medical device.

17. The substrate of claim 16, wherein the silanization layer comprises an array of linear polysiloxanes polymerized from a di-alkoxy silane in the solution and wherein the lubricant comprises one or more of silicone oils, mineral oils, plant oils, and perfluorinated oils.

18. A substrate having a surface, comprising:
    a layer of polyphenol formed on the surface;
    a silanization layer formed directly on the polyphenol layer, the silanization layer comprising an array of straight-chain polysiloxanes having ends anchored to the polyphenol layer and opposite ends extending away from the polyphenol layer, the silanization layer polymerized from a solution including: (i) a polymerizable silane selected from the group consisting of dimethyldimethoxysilane, dimethoxy-methyl (3,3,3-trifluoropropyl)silane, dimethoxy(methyl)octylsilane, diethoxydimethylsilane, (ii) a solvent and (iii) an acid catalyst; and
    a lubricant disposed over the silanization layer.

19. The substrate according to claim 18, wherein the surface is untreated before the layer of polyphenol is formed on the surface.

* * * * *